United States Patent
Fell et al.

(10) Patent No.: US 9,142,989 B2
(45) Date of Patent: Sep. 22, 2015

(54) METHOD OF MINIMIZING INTERRUPTIONS TO IMPLANTABLE MEDICAL DEVICE RECHARGING

(75) Inventors: Roger Fell, Avon Lake, OH (US); Benjamin Cottrill, Cleveland, OH (US); Les Halberg, Valencia, CA (US); Michael Labbe, Twinsburg, OH (US); Joey Chen, Valencia, CA (US)

(73) Assignee: GREATBATCH LTD., Clarence, NY (US)

( * ) Notice: Subject to any disclaimer, the term of this patent is extended or adjusted under 35 U.S.C. 154(b) by 347 days.

(21) Appl. No.: 13/606,921

(22) Filed: Sep. 7, 2012

(65) Prior Publication Data

US 2014/0074185 A1    Mar. 13, 2014

(51) Int. Cl.
| | |
|---|---|
| *A61N 1/37* | (2006.01) |
| *H02J 7/00* | (2006.01) |
| *A61N 1/378* | (2006.01) |
| *H02J 7/02* | (2006.01) |

(52) U.S. Cl.
CPC ............ *H02J 7/007* (2013.01); *A61N 1/3787* (2013.01); *H02J 7/025* (2013.01)

(58) Field of Classification Search
CPC ......... H02J 7/007; H02J 7/025; A61N 1/3787
USPC ...................................... 607/2, 61
See application file for complete search history.

(56) References Cited

U.S. PATENT DOCUMENTS

| | | |
|---|---|---|
| 3,599,071 A | 8/1971 | Lapuyade et al. |
| 3,911,350 A | 10/1975 | Swope |
| 3,970,912 A | 7/1976 | Hoffman |
| 4,045,720 A | 8/1977 | Alexandres |
| 4,082,097 A | 4/1978 | Mann et al. |
| 4,125,802 A | 11/1978 | Godard |
| 4,441,498 A | 4/1984 | Nordling |
| 4,623,597 A | 11/1986 | Sapru et al. |
| 4,670,703 A | 6/1987 | Williams |
| 5,279,292 A | 1/1994 | Baumann et al. |
| 5,314,457 A | 5/1994 | Jeutter et al. |
| 5,325,040 A | 6/1994 | Bogut et al. |
| 5,411,537 A | 5/1995 | Munshi et al. |
| 5,591,546 A | 1/1997 | Nagaura |

(Continued)

FOREIGN PATENT DOCUMENTS

| | | |
|---|---|---|
| GB | 724175 | 8/1950 |
| GB | 1316169 | 5/1973 |

(Continued)

OTHER PUBLICATIONS

European Search Report; Date: Oct. 2, 2014; Reference: PT03113EP; Application No. 13183312.1-1652; Applicant: Greatbatch Ltd.

(Continued)

*Primary Examiner* — Amanda Patton

(74) *Attorney, Agent, or Firm* — Pearne & Gordon LLP

(57) ABSTRACT

A system and method of controlling the charging of the battery of a medical device using a remote inductive charger, with the method utilizing both a relatively fast closed-loop charging control based on a proxy for a target power transmission value in conjunction, and a slower closed-loop control based on an actual measured transmission value to control a charging power level for charging the medical device.

22 Claims, 6 Drawing Sheets

(56) References Cited

U.S. PATENT DOCUMENTS

| | | | |
|---|---|---|---|
| 5,713,939 A | 2/1998 | Nedungadi et al. | |
| 5,948,006 A | 9/1999 | Mann | |
| 6,118,250 A | 9/2000 | Hutchison, IV et al. | |
| 6,181,105 B1 | 1/2001 | Cutolo et al. | |
| 6,227,204 B1 | 5/2001 | Baumann et al. | |
| 6,245,464 B1 | 6/2001 | Spillman et al. | |
| 6,348,777 B1 | 2/2002 | Brown et al. | |
| 6,415,186 B1 | 7/2002 | Chim | |
| 6,476,584 B2 | 11/2002 | Sakakibara | |
| 6,553,263 B1 | 4/2003 | Meadows et al. | |
| 6,772,011 B2 * | 8/2004 | Dolgin | 607/61 |
| 7,208,915 B2 | 4/2007 | Kubota et al. | |
| 7,505,816 B2 | 3/2009 | Schmeling et al. | |
| 7,711,419 B2 | 5/2010 | Armstrong et al. | |
| 7,805,200 B2 | 9/2010 | Kast et al. | |
| 7,818,068 B2 | 10/2010 | Meadows et al. | |
| 7,865,245 B2 | 1/2011 | Torgerson et al. | |
| 7,962,222 B2 | 6/2011 | He et al. | |
| RE42,682 E | 9/2011 | Barreras, Sr. et al. | |
| 8,170,681 B2 | 5/2012 | Jimenez et al. | |
| 8,260,432 B2 | 9/2012 | DiGiore et al. | |
| 8,401,663 B2 | 3/2013 | Aghassian | |
| 8,401,664 B2 | 3/2013 | Chow et al. | |
| 8,428,712 B2 | 4/2013 | Davis et al. | |
| 8,463,392 B2 | 6/2013 | Aghassian | |
| 8,473,066 B2 | 6/2013 | Aghassian et al. | |
| 8,594,804 B2 | 11/2013 | Joshi | |
| 2004/0039423 A1 | 2/2004 | Dolgin | |
| 2006/0247738 A1 | 11/2006 | Schmeling et al. | |
| 2008/0027500 A1 | 1/2008 | Chen | |
| 2009/0149917 A1 | 6/2009 | Whitehurst et al. | |
| 2009/0326611 A1 | 12/2009 | Gillbe | |
| 2010/0010582 A1 | 1/2010 | Carbunaru et al. | |
| 2010/0256709 A1 | 10/2010 | Kallmyer | |
| 2010/0256710 A1 | 10/2010 | Dinsmoor et al. | |
| 2010/0277128 A1 | 11/2010 | Tam et al. | |
| 2010/0305662 A1 | 12/2010 | Ozawa et al. | |
| 2011/0071597 A1 | 3/2011 | Aghassian | |
| 2011/0127970 A1 | 6/2011 | Wang et al. | |
| 2011/0181241 A1 | 7/2011 | Badger | |
| 2011/0190853 A1 | 8/2011 | Dinsmoor et al. | |
| 2012/0074893 A1 | 3/2012 | Cole | |
| 2012/0119699 A1 | 5/2012 | Carbunaru et al. | |
| 2012/0161945 A1 | 6/2012 | Single et al. | |
| 2012/0191151 A1 | 7/2012 | Kameli | |
| 2012/0239118 A1 | 9/2012 | Ozawa et al. | |
| 2012/0277831 A1 | 11/2012 | Joshi | |
| 2013/0096653 A1 | 4/2013 | Winstrom | |
| 2013/0165993 A1 | 6/2013 | Aghassian et al. | |
| 2013/0193912 A1 | 8/2013 | Bornhoft | |

FOREIGN PATENT DOCUMENTS

| | | |
|---|---|---|
| JP | 1006384 A | 1/1989 |
| JP | 1014881 A | 1/1989 |
| JP | 64002258 A | 1/1989 |
| JP | 3192663 A | 8/1991 |
| JP | 6203829 A | 7/1994 |
| JP | 6349493 A | 12/1994 |
| JP | 8185851 A | 7/1996 |
| WO | 2004002572 A1 | 1/2004 |
| WO | 2010059097 A1 | 5/2010 |

OTHER PUBLICATIONS

Extended European Search Report; Date: Nov. 21, 2013; Reference: PT03114EP; Application No. 13183319.6-1652; Applicant: Greatbatch Ltd.; Place of Search: Munich; Date of Completion of Search: Nov. 13, 2013.

* cited by examiner

METHOD OF MINIMIZING INTERRUPTIONS TO IMPLANTABLE MEDICAL DEVICE RECHARGING

CROSS-REFERENCES TO RELATED APPLICATIONS

This application is related to U.S. patent application Ser. No. 13/607,037, filed concurrently with this application and incorporated herein by reference. This application is also related to U.S. patent application Ser. No. 13/606,868 filed concurrently with this application and incorporated herein by reference.

BACKGROUND

This application relates generally to the recharging of batteries in electrically powered implantable medical devices (IMDs), such as Active Implantable Medical Devices (AIMD). More specifically, this application relates to efficiently recharging batteries in electrically powered implantable medical devices (IMDs) via inductive charging through the skin of a patient while the patient is mobile or otherwise active.

This application relates generally to the recharging of the power supplies of electrically powered implantable medical devices (IMDs), such as AIMDs including examples like pacemakers, neurostimulators, cochlear implants, among others. This includes the use of rechargeable power supplies that are charged through the skin of the patient using inductive charging techniques. Newer medical implants, such as neurostimulators, can consume large amounts of power in comparison to older devices, such as pacemakers, which tend to provide lower power signals. Thus, some current and future medical implants will require more frequent charging than their older counterparts. Some current neurostimulators require that the implant be recharged at intervals of every two weeks or less, and thus patients expend a considerable amount of time charging their IMDs.

Charging times for the rechargeable power supplies for IMDs are limited by a number of factors. In the past, battery chemistries have limited the rate at which an implant could be recharged. However, with the introduction of newer lithium ion batteries and other chemistries, battery chemistry is no longer the primary limitation to recharging of IMDs. During charging, some of the energy that is inductively transferred to the IMD is converted into heat instead of being converted into electricity for charging. Eddy currents form on the housing of the IMD during charging and these currents dissipate as heat. Also, some of the energy used in the recharging circuitry within the IMD is also converted into heat.

Furthermore, the traditional recharging process for IMDs requires that a user sit relatively still during the recharging period to maintain effective alignment between the IMD and an external charging unit which provides the inductive (power) signal that is converted into electricity for charging the IMD batteries. Movement by the user can cause a slight misalignment between the external charger transmitting coil and the internal charger receiving coil, which can cause prevent an effective coupling, reducing the ability to quickly charge the batter if not compensated for. Traditionally, this misalignment was minimized by avoiding user activity during the charging period, but besides often being ineffective, this is inconvenient for the user. It is desirable to allow the user to be more active during the charging process, in order to avoid inconveniencing the users.

Furthermore, because different users will desire to have different movement or activity levels during charging, and thus will likely have different alignment issues arise during the recharging process, it is desirable to have a charging process that is flexible enough to accommodate these differences in a cost effective and flexible manner.

SUMMARY

Provided are a plurality of example embodiments, including, but not limited to, a method for charging a rechargeable battery in a medical device using an external charger, said method comprising the steps of:

wirelessly transmitting a power signal from the external charger to the medical device, where the power signal includes power for charging the rechargeable battery;

in the medical device, measuring a value of a first variable relating to the power signal received by the medical device from the external charger;

in the external charger, measuring a value of a second variable relating to the power signal transmitted by the external charger to the medical device; and adjusting the power signal transmitted from the external charger to the medical device at least partly based on values of both the first variable and the second variable.

Also provided is a method for charging a rechargeable battery in an implantable medical device using an external charger, the method comprising the steps of:

inductively transmitting power from a primary coil of the external charger to a secondary coil of the medical device;

in the medical device, measuring a value of a rectified voltage of the secondary coil obtained from the power received from the external charger;

periodically transmitting the value of the rectified voltage or a derivation thereof from the medical device to the external charger;

in the external charger, determining a value of the power transmitted by the external charger to the medical device; and in the external charger, adjusting the power transmitted from the external charger to the medical device at least partly based on the determined value of the power transmitted by the external charger to the medical device, wherein when the value of the rectified voltage or derivation thereof is received by the external charger, the step of adjusting the power transmitted from the external charger to the medical device is based on the value of the rectified voltage or derivation thereof as compared to a desired value.

Still further provided is a method for charging a rechargeable battery in an implantable medical device using an external charger, the method comprising the steps of:

inductively transmitting power from a primary coil of the external charger to a secondary coil of the medical device;

in the medical device, measuring a first variable representing the power received from the external charger;

periodically transmitting the value of the first variable from the medical device to the external charger;

in the external charger, determining a value of a second variable representing the power transmitted by the external charger to the medical device;

in the external charger, adjusting the power transmitted from the external charger to the medical device at least partly based on the determined value of the second variable; and in the external charger, statistically analyzing of some number of the values of the first variable received from the medical device, wherein when the value of the first variable is received by the external charger, adapting the step of adjusting the power transmitted from the external charger to the medical device based on the value of the rectified voltage as compared to a desired value of the rectified voltage that is determined at least partly based on a result of the statistically analyzing step.

Also provided is a method of providing a neurostimulation therapy to a patient, comprising the steps of:

providing an implantable medical device having a rechargeable battery and being implanted in a patient;

using the implantable medical device for driving at least one electrode implanted in the patient to stimulate at least one nerve of the patient; and recharging the battery using an external charger, the recharging including the steps of:

wirelessly transmitting power from the external charger to the medical device, in the medical device, measuring a value of a first variable relating to the power received by the medical device from the external charger, in the external charger, measuring a value of a second variable relating to the power transmitted by the external charger to the medical device, and adjusting the power transmitted from the external charger to the medical device at least partly based on values of both the first variable and the second variable.

Further provided is a system for implementing any of the above methods with the system comprising the external charger and the medical device.

Also provided are additional example embodiments, some, but not all of which, are described hereinbelow in more detail.

BRIEF DESCRIPTION OF THE DRAWINGS

The features and advantages of the example embodiments described herein will become apparent to those skilled in the art to which this disclosure relates upon reading the following description, with reference to the accompanying drawings, in which.

DETAILED DESCRIPTION OF THE EXAMPLE EMBODIMENTS

The Implanted Device and External Charger Hardware

Figure 1:
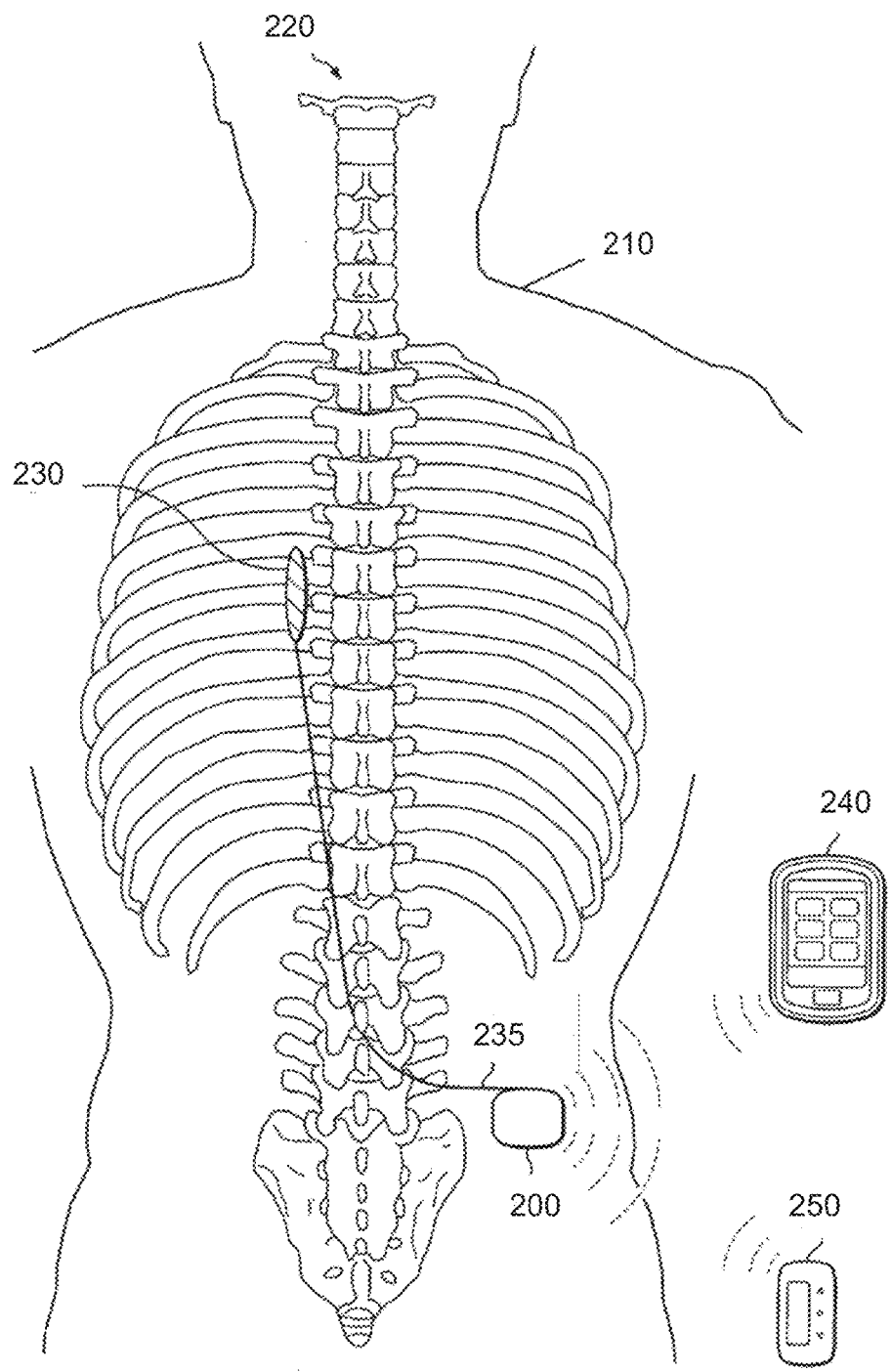
FIG. 1 is a schematic of an example implantable medical device installed in a patient for stimulating the spine of the patient.

FIG. 1 shows an example application of an implanted medical device (IMD) 200 for providing spinal cord stimulation (SCS) to a patient 210. In this example, the IMD 200 is an implantable pulse generator (IPG) shown implanted in a patient for providing pulse neurostimulation of the patient's spinal cord of the spine 220, such as for the purpose of providing pain therapy, through the use of implanted electrodes 230 that are situated in areas to stimulated desired nerves. The electrodes 230 are connected to the IPG via a set of electrode leads 235. The IPG 200 is electrically powered and should be comprised of a rechargeable power supply, such as an internal rechargeable battery, a controller, pulse generation electronics, protection/conditioning circuits, and a header/connector for connecting to an electrode array.

When used for pain therapy, the leads and electrodes may be positioned anywhere along the spine to deliver the intended therapeutic effects of spinal cord stimulation in the desired region of the spine. The distal end of the lead with its accompanying electrodes may be located along the epidural space and adjacent a desired portion of the spinal cord using well-established and known techniques for implanting and positioning SCS leads and electrodes, and the IPG 200 may be programmed using a clinician programmer 240 or other type of controller 250 (such as a patient controller FOB), as desired.

Figure 2:
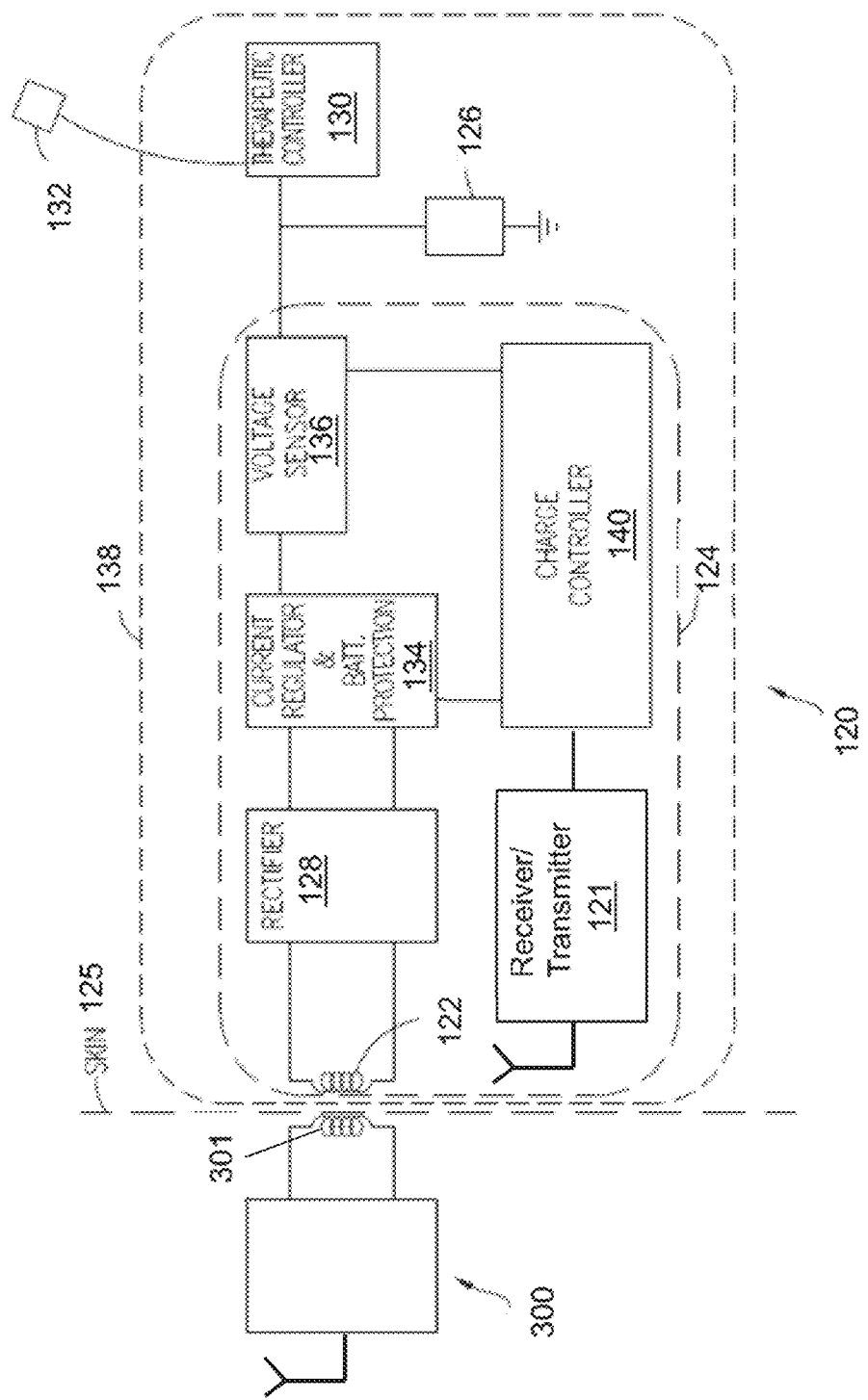
FIG. 2 is a block diagram showing an example implantable medical device being charged by an example external charger.

FIG. 2 shows a simplified example embodiment of an IMD 120 connected to an external charger 300, where the charger 300 and the IMD 120 are inductively linked across the skin of the patient. This inductive link transfers energy from the external charger 300 and the IMD 120 using an electromagnetic field that operates much as an electrical transformer does.

The inductive signal is transmitted by the external charger 300 and is received through the patient's skin 125 by the IMD 120 via an implant coil 122 of the recharging circuitry 124. The recharging circuitry 124 recharges the rechargeable battery 126, which may be a lithium ion rechargeable battery, for example. The recharging circuitry 124 converts the portion of the inductive power signal received from a primary coil 301 of the external charger 300 and provides the constant current charging signal to the rechargeable battery for recharging. The recharging circuitry 124 also includes rectifying circuitry such as a rectifier 128 that converts the inductive power signal received from the coil 122 into a direct current (DC) signal. A therapeutic controller 130 can be used for providing a therapeutic electrical signal to a patient using a therapeutic lead 132.

The inductive link between the IMD 120 and the external charger 300 can be used for communications purposes, such as by multiplexing a communication signal on the inductive power signal, which can be decoded by the devices respectively. Such a communication path tends to be slow and of low bandwidth. Alternatively, the IMD 120 can include dedicated communication circuitry, such as a receiver/transmitter 121 that communicates with a respective receiver/transmitter in the external charger 300, allowing higher speed and higher bandwidth communication via a separate communication path. The communication circuitry will provide the communication signal to the charge controller 140, as shown, or directly to the IPG controller 130. As a further alternative, the IMD communication circuitry utilized for connecting to external controllers (e.g., the therapeutic controller 130)

could be utilized for this communication function by being adapted to directly communicate with the external charger.

However, because this communication pathway is to be utilized by the charging process to improve charging efficiency, the most useful scenario is to utilize a direct communication path between the external charger 300 and the charge controller 120, such as via the receiver transmitter 121.

The recharging circuitry 124 also includes a current regulator and battery protection circuitry 134 that converts the DC output from the rectifier 128 into a constant current charging signal or a constant voltage charge signal. The recharging circuitry 124 also includes a voltage sensor 136 that periodically monitors the voltage of the rechargeable battery 126. A charge controller 140 uses the voltage measured by the voltage sensor 136 to control the current regulator and battery protection circuitry 134 to provide a particular current or voltage signal for charging. The IMD 120 can also include a temperature sensor (not shown) that detects the temperature within the implant, on the implant housing 138. In some embodiments, the temperature sensor may consist of two or more temperature sensors located at different locations within the implant.

Figure 3:
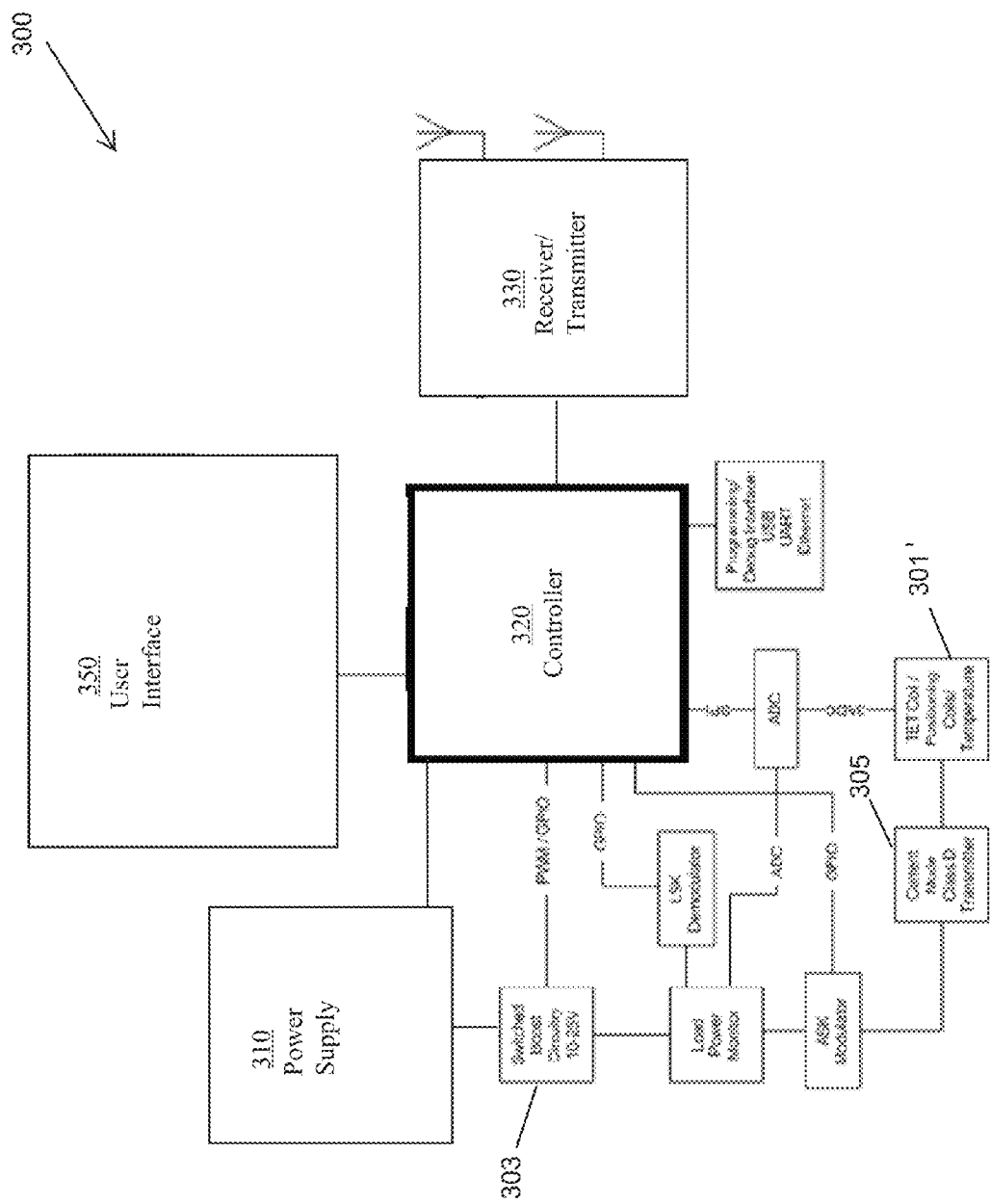
FIG. 3 is a block diagram showing an example external charger.

As shown in FIG. 3, the external charger 300 has a power supply portion 310 and a primary coil support circuit 301' including a primary coil (not shown in FIG. 3) for transmitting the charging power signal to the secondary coil 122 of the IMD 120 (see FIG. 2). The external charger 300 also has a controller 320 for controlling the device, a receiver/transmitter 330 for wirelessly communicating with the IMD receiver/transmitter 121 (see FIG. 2), and a user interface 350 for allowing user interaction and command and data input into the external charger 300.

In a typical configuration, the inductive link between the IMD 120 and the external charger 300 is comprised of an AC signal on the primary coil 301 (of external charger 300) side running in the KHz or MHz range, while the secondary (IMD 120) side has a corresponding receiver coil 122 tuned to the transmission frequency, with its output passed through the rectifier 128 to the implantable device's power management and recharging circuitry. For many implantable systems, the voltage required to run the implantable power management circuitry remains constant, thus a minimum rectified voltage ($V_{rect}$) is required. However, as the load seen by the internal battery charging circuitry 124 changes (for example due to radio transmission or therapy delivery), or as the coils change in alignment due to patient Activities of Daily Living (ADL), the amount of power required to maintain that voltage may change. If power is reduced due to movement or other noise in the system, it may drop below the threshold voltage required to drive the recharge circuitry, and charging will cut out. Thus as the implant's power demands change, or as the primary and secondary coils change in alignment due to patient Activities of Daily Living (ADL), the amount of power transmitted by the external charger must also change correspondingly to maintain charging.

Furthermore, it is desirable to monitor $V_{rect}$ in order to evaluate the quality of that signal. This voltage measurement can be done in the rectifier 128, or in the current regulator and battery protection circuitry 134, for transmittal to the charge controller 140. As will be discussed below in detail, $V_{rect}$ is both monitored and controlled to improve the charging efficiency and to allow the user greater mobility during the recharging process.

For example, the $V_{rect}$ voltage detected across the rectifier may be used as a factor for starting and halting charging, and also as a factor for adjusting the strength of the inductive power signal provided by the external charger. For example, the recharging circuitry may not start the charging process until $V_{rect}$ reaches a threshold value (e.g., at least 6.4 volts) and the charging process can be stopped if the $V_{rect}$ goes below a minimum value (e.g., 5.7 volts). Furthermore, the system can adjust the inductive power signal to equal a voltage target (e.g., 7.0 volts) while the charger charges the rechargeable battery supply. The voltage target is chosen to provide an overhead buffer (in this case, of 1.3 volts) that allows the system to continue charging even when movement causes some misalignment by preventing the voltage from dropping below a certain amount (e.g. 5.7 volts).

Interruptions to charging can be reduced by increasing the tolerance to momentary minor misalignments of the primary coil (of the external charger) with the secondary coil (in the IMD). A simple method of increasing this tolerance is to increase the overhead power delivered to the implant at the expense of efficiency. By delivering more power than needed, such as by using an overhead voltage, some energy is unfortunately dissipated as heat, both in the charging circuitry and in the eddy currents induced in the implant's enclosure. Thus, it is desirable to minimize this overhead as much as possible. Methods of controlling the charging process are discussed in detail in the following sections.

While an overhead voltage provides a margin that helps to prevent cut outs, which would otherwise increase charging times, as suggested above, this margin leads to a surplus power transfer that has the potential disadvantage of having to be dissipated in resistors of the recharging circuitry of the IMD, and as IMD eddy currents, thus causing increased heat production in the IMD. This increase in heat, when large enough to raise the temperature of the IMD, may cause safety circuitry to force a reduction in the charging rate of the rechargeable power supply. Therefore, there is a tradeoff between having a high overhead voltage (e.g., a large margin) that prevents charging cut outs and the excess heat associated with these high overhead voltages. This tradeoff can be mitigated by providing more detailed control of the charging process, especially by monitoring and controlling $V_{rect}$.

Charging Processes

One method of maintaining the above mentioned overhead is accomplished by using an open-loop power control system that delivers a fixed power sufficient to avoid cut-outs (where the power drops too low to continue charging the battery) while the output is within a prescribed range. While this approach may be engineered to work for the worst case set of parameters (e.g., distance and misalignment) the major disadvantages of this approach are the inefficiency of excess power being converted to heat, and that there is no indication when it has failed (e.g. output is out of range) due to lack of feedback from the implant.

A second method would be a first closed loop system that adjusts the power based on a determination of the level of coupling that is detected between the primary and the secondary coils. This feedback loop may be implemented entirely at the external charger (although it could also be done at the IMD, with the resulting overhead of having to communicate the result to the external charger). The external charger then raises or lowers the transmitted power level as necessary to maintain a desirable overhead. Although this system is potentially fast to react when implemented on the external charger, it's accuracy is limited because the load on the primary coil is only a rough proxy of the level of coupling. For convenience, this can be called the "fast-loop" control approach.

Another more accurate (and thus more efficient) second closed-loop method where a higher set-point than the cutout power is maintained by monitoring what is actually occurring in the IMD to accurately determine when transmitted power should be adjusted. However, for a number of reasons, it may be desirable that as much of the processing be offloaded to the external charger as possible, although some overhead for transmitted information from the IMD to the external charger will be required. Because of the monitoring and transmitting overhead of the slow-loop system (the transmission speed tends to be relatively slow), this second closed-loop control approach tends to have a slower response time than the fast-loop system, but it is more accurate and thus more efficient because it looks at the actual power consumption of the IMD being charged, and thus can avoid too much waste heat by not maintaining the power any higher than necessary to avoid cut-off. For convenience, this can be called the "slow-loop" control approach.

Finally, a combination of the fast-loop and slow-loop systems can be utilized to get the best of both approaches, the higher accuracy of the slow-loop system, while also getting the faster response times of the fast-loop system. However, this better response and higher accuracy comes at the cost of implementing two control approaches, adding the communications and processing overhead of the slow-loop approach, while also adding the processing overhead of the fast-loop approach. For a number of reasons, it is desirable to place this processing in the external charger whenever possible.

It is desirable to improve efficiency and reduce waste heat using the slow-loop method by minimizing the overhead power (i.e. finding an optimal power set-point) as low as possible but by still maintain charging at a high service level during ADL, while balancing that service level with safe temperature constraints. Note that efficiency is lost both by having a power setpoint that is too high, leading to eddy currents and wasted heat generation, and by having a power setpoint that is too low, leading to cut-outs in charging, which then requires costly overhead and time to restart the charging process.

Furthermore, as the user goes about his ADL, and/or activates the IMD, or as the IMD battery gains charge, and/or other changes (such as temperature changes, user physical changes such as state of hydration, and even environmental parameters will change such as outside temperatures) the optimum device settings will change and thus need to be updated. Use of a fast-loop system can thus drift out of optimum settings as these parameters change, whereas the slow-loop approach can take them into account. Furthermore, settings are not universal among different uses, as the IMD parameters will depend on many variable tied to a particular user, such as where the IMD is implanted, the user's physiology, etc. will all impact device operation, and such variable may change somewhat over time.

Hence, a compromise is desired that can avoid both extremes, thereby leading to optimum efficiency and user convenience. Furthermore, heat generation is a problem itself that may be monitored and mitigated, see co-pending U.S. patent application Ser. No. 13/607,037 filed concurrently with this application and incorporated herein by reference.

As discussed above, any of two closed loop and/or an open-loop system can be used in an implantable system to maintain accurate power delivery. One or both of the closed-loop approaches would be preferable because of better accuracy and other improvements. Hence, target power delivery in a practical implant recharging system may be maintained by several means including:

1) Slow-Loop: As discussed above, control can be based on actual measured values in the IMD. A value representing power received may be measured on the implant (IMD) and fed back to the charger (such as via the inductive link, or a separate RF channel, such as Bluetooth, WiFi, DECT, MICS, or some other RF link). For example, in some implantable systems, the voltage required to run the implantable power management circuitry remains constant, thus a minimum rectified voltage ($V_{rect}$ as discussed above) is maintained, including an overhead buffer being added to define a target value of $V_{rect}$. The advantage of a back-telemetry-based method is that it is a direct measurement of the target variable, and thus accurate. However, an issue with this method is that the telemetry may take anywhere from milliseconds to seconds depending on data transfer rate, leading to a potentially slow response time;

2) Fast-Loop: As also discussed above, a second method that can be used is to monitor a power transmitted on the charger side as a proxy for indirectly measuring power received by the implant IMD. For example, by monitoring the current and voltage of the circuitry driving the primary coil in the external charger, the system might attempt to maintain a constant load on the charger by controlling the transmitted power. The advantage of this method is that no back-telemetry is required, and thus the charger logic may adjust power at a relatively fast rate based only on internal measurements. The main disadvantage of this method lies in its indirect nature, as the charger is adjusting power delivery based on a proxy of what is received rather than what is actually received by the implant, leading to less accuracy of control; and 3) A Hybrid Approach: A more optimum approach (at, of course, greater expense of processing overhead and cost) is to use a control scheme having both a fast-loop portion and a slow-loop portion, leading to a system that combines the fast response time of the fast-loop system, but that can be regularly updated to improve accuracy using the slow-loop system. An example of such an approach is shown in the flow chart of FIG. 4.

In FIG. 3, a PWM output from the controller 320 is used to control the boost converter 303, changing the duty cycle to ultimately achieve a given output voltage ($V_{boost}$). This voltage ($V_{boost}$) is the means of controlling primary coil output. A shunt resistor in line with that output provides a means of measuring the current output from that boost converter at any given point in time. This current can be measured when the output expected to be closest to the target value (at the beginning of the slow loop), and the target power can computed by multiplying $V_{boost}$ and load current. As load on the external charger's primary coil changes, the current mode class D amplifier 305 will draw more or less power while $V_{boost}$ remains at its set value. Load power at any given time can be computed very quickly by multiplying the current setpoint of $V_{boost}$ by the measured load current. As load changes, $V_{boost}$ can be adjusted proportionally to the difference between the last measured power and the target power.

The external charger 300 periodically sends status requests to the IMD 120 (e.g., an IPG) as shown in FIG. 2. When the IMD 120 receives this request via its transceiver 121, it measures the voltage at the rectifier 128 using an analog to digital converter. The IMD 120 sends its response over the transceiver 121 to the external charger 300, where it is received by the charger's MICS transceiver 330. The controller 320 connected to the transceiver 330 compares the target rectified voltage to that reported by the IPG, and the charger controller 303 adjusts the output of ($V_{boost}$) proportionally to the error to move $V_{rect}$ toward $V_{rect,target}$, which is the target value to maintain for $V_{rect}$. The error adjustment may include a gain multiplier to adjust the aggressiveness of the adjustment and prevent overshoot or undershoot, for example, as in the following equation:

$$V_{boost,new} = V_{boost,previous} * [1 + gain * (V_{rect,target} - V_{rect,measured}) / V_{rect,measured}]$$

The hybrid control approach basically combines both of the above fast-loop and slow-loop closed-loop approaches by running the fast-loop system continuously, while updating the parameters regularly based on the time constant required to obtain the data from the IMD via the telemetry link (which can be a separate RF link or via the inductive link, as described above, the separate RF link typically being faster) by using the slow-loop approach. Thus, a more optimal power delivery rate may be achieved by preventing cutout of recharging circuitry on an active implantable medical device.

Thus, as shown in the simplified example flow chart of FIG. 4, referring to the example hardware of FIGS. 2 and 3, the hybrid control system can be implemented as follows: First, a minimum value of $V_{rect}$ is determined. This minimum is the value under which the implantable circuitry will cut out. This may be inherent to the design of the power management circuitry, or based on the charging control. Then, a target $V_{rect}$ that will prevent cutout for the target percentage of patients for the target amount of time (for example, 90% of the patients will have no cutouts 90% of the times they charge at the target $V_{rect}$ volts) is chosen. More complex means of choosing target values for $V_{rect}$ are described in more detail below.

First, the charging process begins 3001 and the external charging device 300 primary coil 301 is activated 3002 to transmit power inductively to the IMD (IPG) secondary coil 122 so that the charger begins delivering power. While delivering power, the PPC queries the IPG for the current value of $V_{rect}$. That value, $V_{rect,measured}$, is transmitted to the external charger from the IPG 3003 by a communications link. This step 3003 begins the slow-loop control process.

It is desirable that the charger controller 303 of the external charger 300 perform the calculations, whenever possible, to avoid processing overhead requirements on the IPG. Thus, for this example, the charger controller 303 adjusts power output by adjusting the charging coil output voltage 3004 to move $V_{rect}$ toward $V_{rect,target}$, which is the target value to maintain for $V_{rect}$. This can be accomplished by adjusting a control value ($V_{boost}$) by an amount proportional to the error, i.e. the difference of $V_{rect,target}$ and $V_{rect,measured}$ as follows:

$$V_{boost,new} = V_{boost,previous} * [1 + gain * (V_{rect,target} - V_{rect,measured}) / V_{rect,measured}]$$

This adjustment may be accomplished using proportional control, or it may be as complicated as using a full Proportion Integration Differentiation (PID) controller for the external charger controller 320. For this example, simple proportional control is described but a PID controller would operate similarly. An acceptable controller could include any single-board, off-the-shelf computer module with any necessary support chips (including memory for storing data and programs) and the proper I/O pins using an embedded operating system such as Windows CE, for example. This controller can include a USB and display controller, and can execute control routines (such as may be written using any acceptable programming language, such as a variant of C like C#, for example) to implement any of the described control processes. Likewise, the controllers 130 and 140 in the IMD may be off-the shelf programmable controllers with the appropriate support chips (e.g., memory) and any necessary I/O pins.

Alternatively, any of these controllers could be custom fabricated to the desired parameters, if desired, in any manner known in the art.

The external charger 300 measures power transmitted through primary coil to establish a "fast loop" set point target 3005. In this example this is done by measuring the current and the voltage on the primary coil 301. Other approaches may be used, such as by providing a secondary field measurement coil that is built into the charger, for example. This provides a measurement of the power being transmitted by the external charger 300, which provides an indirect measurement of the approximate power being absorbed by the secondary coil 122 at the desired target for $V_{rect}$, and thus provides a useful benchmark for performing the fast-loop control portion of the charging process, which starts after step 3005.

Figure 4:
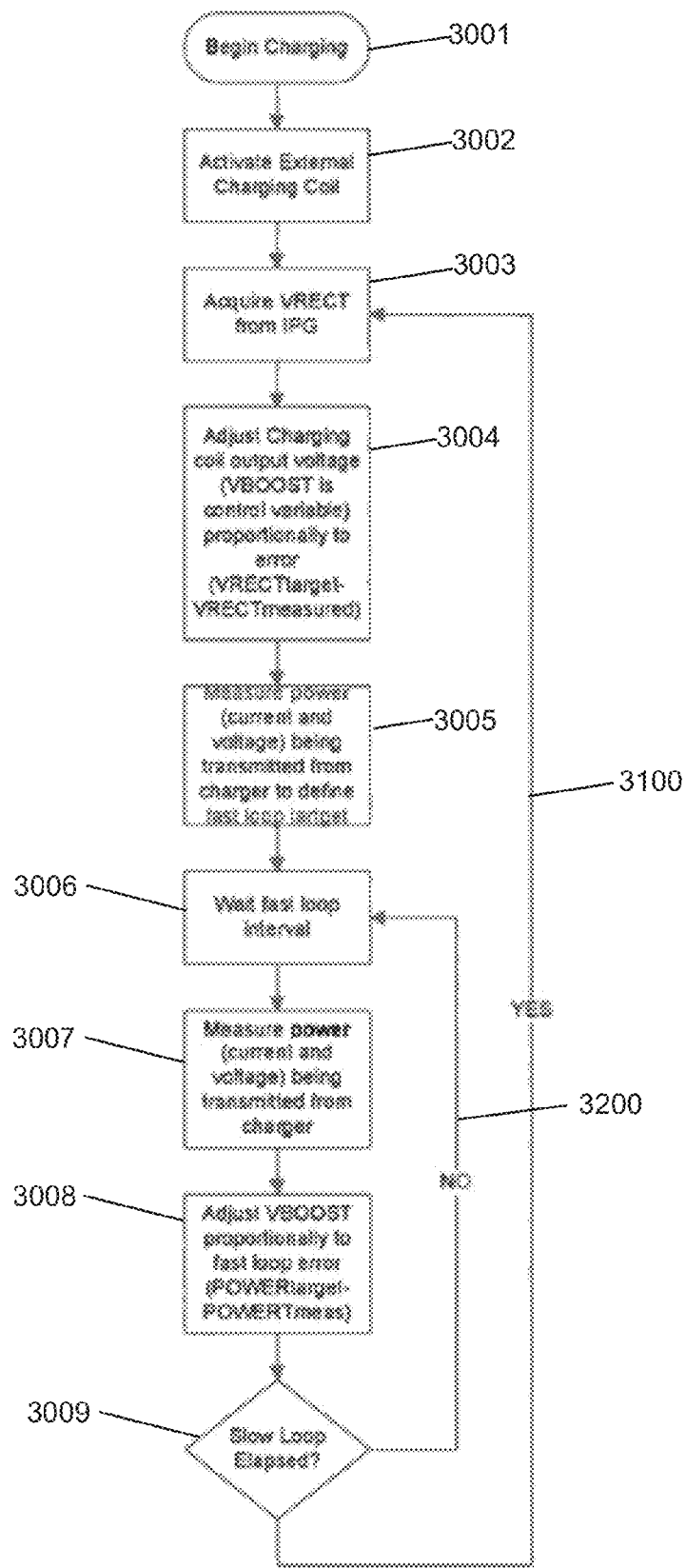
FIG. 4 is a flow chart showing an example control loop of an example charging process.

Steps 3006-3009 of the flow charge of FIG. 4 implement the fast-loop control loop 3200 until the next value of $V_{rect,measured}$ is ready to be used by waiting for an interval of time 3006 to reenter the slow-loop control loop 3100 to update the values for continuing the fast-loop control loop 3200. The external charger 300 measures its output voltage and current in the primary coil 301 which determines the power being transmitted by the coil 3007. The external charger controller 320 then adjusts the power output by the charger 300 (in this example case by changing $V_{boost}$, which is directly proportional to primary coil 301 voltage) to bring it closer to the power output set point by determining the error value as described above, and adjusting the Vboost and thereby adjusting primary coil output accordingly. This fast-loop control loop 3200 waits until the sufficient (predetermined) interval of time has expired 3006 to re-enter the fast loop interval 3200 (until the slow loop interval has elapsed 3009), upon which the external charger then repeats the process of querying the IPG to obtain the updated value of $V_{rect,measured}$ to update the coil output as described above, establishing a new fast loop set-point 3005 continuing the process of adjusting output power and entering a new fast-loop control loop 3200.

In this manner, the values of the fast-loop control are regularly updated using the slow-loop control, keeping the entire control process from diverting too far from optimum settings. Determining the best approach for determining and adjusting the parameters utilized by the above control loops is further developed in the following section.

Methods of Determining Optimum Control Parameters

As discussed above, it is desirable to minimize overhead power delivery for a broad range of patient use conditions in a charging system for an active implantable medical device. It is desired to optimize the target power delivery over the course of the recharge process during a charging session so that a minimum overhead is required for a high level of service while charging, while balancing that service level with safe temperature constraints, while adapting to changing conditions and operational parameters, and while fully charging the battery in an optimized manner. This can be done by using a parameter determination process for determining control parameters for optimizing the power delivery as described below.

A number of control scenarios are discussed in the above section, including open-loop, two forms of closed-loop (the fast-loop and slow-loop), and a hybrid system that uses both closed loop methods. A more optimal power delivery rate may be achieved by adjusting the target values of the parameters used in the disclosed closed loop systems (both stand-alone, and hybrid) to the minimum levels required for a desired level of service, and by adjusting the levels based on a status of the medical device, or its battery. In a system with a fixed battery charging rate, this reduced overhead means less energy is being turned into heat, but is instead conserved to actually charge the battery, reducing charge times. In a system where the implanted battery's recharge rate is variable (such as to maintain desired temperature targets or to maximize battery life and reduce recharge times), a higher recharge rate may be maintained for a given amount of power delivered by the charger at some times.

This method does not actually guarantee that power will be maintained as patients go about their ADL under all circumstances, as perfection is not possible in a cost-effective, compact design. Instead, this method it allows an effective lower rate of power delivery while maintaining a high probability that charging will be maintained as needed at a given time (such as by avoiding drop-outs).

Target power delivery in a control scheme using a closed-loop implant recharging approach that uses data obtained from the IMD may be maintained by several means. For example, a value of a charging parameter representing a level or amount of power received or otherwise reflecting the received charging power signal may be measured on the IMD and fed back to the charger for use in adjusting the transmitted power. Above, the value of the charging parameter $V_{rect}$ is used for this purpose, voltages in other locations of the charging path, or charging currents rather than voltages, might be alternatively, or concurrently, monitored. Monitoring the value of the $V_{rect}$ charging parameter is useful because it is relatively easy to detect, and in some implantable systems, the voltage required to run the implantable power management circuitry remains substantially constant, thus a minimum rectified voltage $V_{rect}$ can be used with some overhead buffer added to define a target value of $V_{rect,target}$. In the closed-loop control discussed above, the value $V_{rect,measured}$ is sent to the external charger on a regular basis for maintaining this target value of $V_{rect,target}$. From these values, an error can be determined to adjust the power transmitted by the external charger 300.

Furthermore, as discussed above, a value of a parameter on the charger side may be monitored as a proxy for power delivered for use in a fast-loop control approach. For example, by monitoring the current and voltage of the circuitry driving the primary coil 301, the system might attempt to maintain a constant load on the charger.

However, for either of these approaches, or for the hybrid approach combining both the fast-closed-loop and slow-closed-loop methods discussed above, finding the optimal target value for setting the primary coil 301, and/or for setting $V_{rect,target}$ is a challenge.

For any given patient during any given instance of recharging, the overhead power requirement to maintain a high level of service (for example, to maintain charging without cutouts 95% of the time) may vary depending on the patient's ADL, or the current status of the IMD, or environmental factors, among other parameters. Thus it is desirable to find, as best as possible, the optimal target for total power delivered at a given time rather than impose a one-size fits all overhead. A basic example method of identifying this target value is as follows:

While the charger works to maintain the desired target value(s), it can monitor either the rate of change of the target variable (the charging parameter $V_{rect}$ in the slow-loop control example), or the rate at which it changes the control variable (charger power output in the fast-loop control example) in order to determine how much variability in coupling is actually present in the link.

As variability in the link is increased or decreased, target variable in the system may be increased or decreased correspondingly above some minimum threshold in order to maintain a given service level. Thus, the target values can be varied based on the variability in the actual operating values at any given time. This means that in periods of relative stability (perhaps the patient is watching television in a cool environment), the overhead power can be reduced, whereas in periods of low stability and rapid change (such as when the patient is active, or is adjusting therapy output), a higher overhead power is maintained to ensure a good response to load changes.

Furthermore, in order to meet temperature constraints, the service level may be further varied dependent on the delta between implant temperature and safe implant temperature limit.

Figure 5:
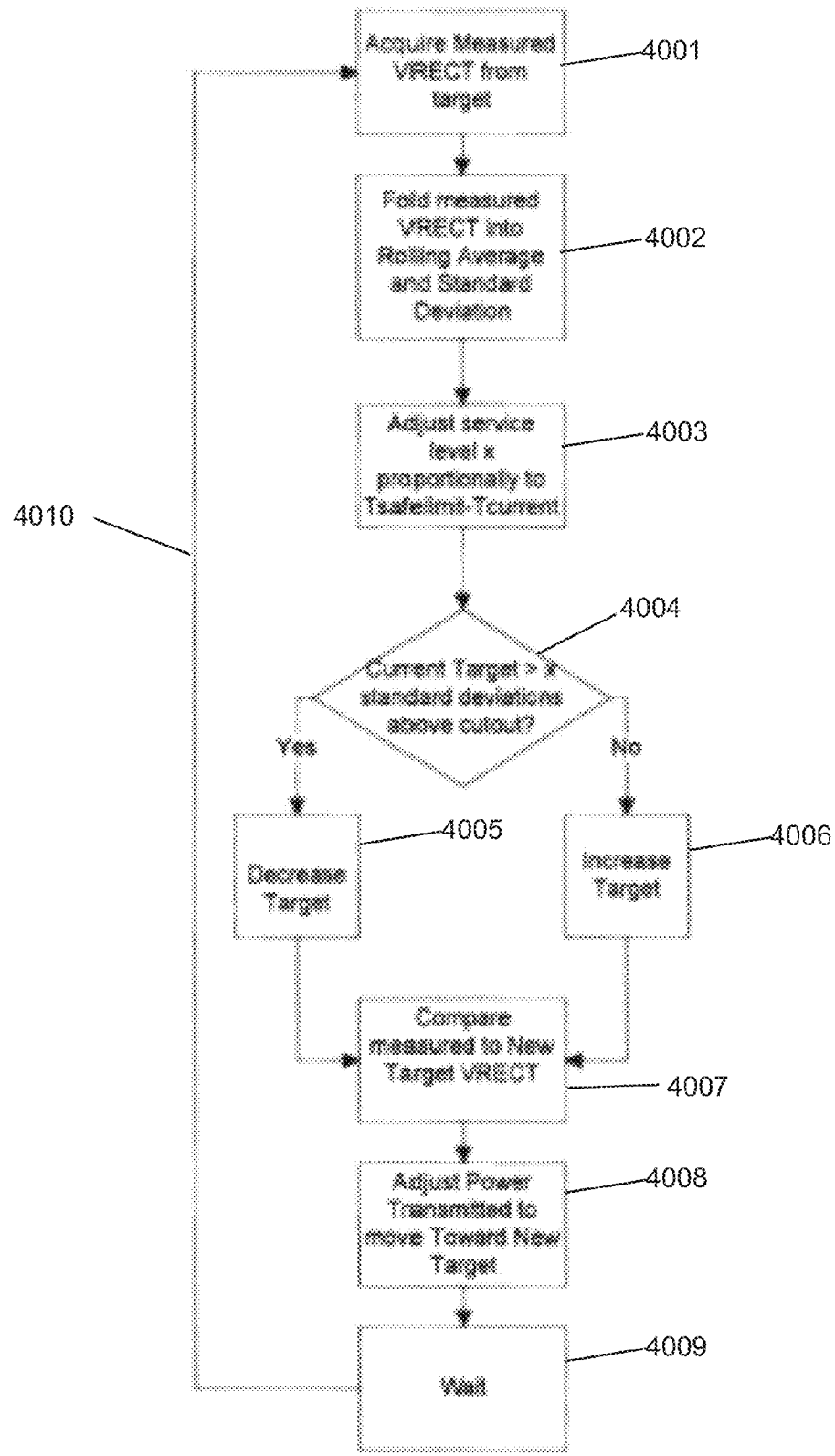
FIG. 5 is a flow chart showing an example parameter determination process for determining control parameters that can be used for the example control loop.

FIG. 5 is a flow chart of an example algorithm that uses this proposed approach to adjust the target parameters based on detected rates of change. Generally, this algorithm will be implemented on the charge controller 303 of the external charger 300 to avoid over taxing the controller of the IMD 120, although in some situations the controller 140 (or alternatively controller 130) of the IMD may be preferred for this function. This approach is described as follows:

Acquire a value for $V_{rect,measured}$ from the IMD 4001. Generally when first started, an initial minimum value $V_{rect,min}$ of $V_{rect,target}$ is generally chosen to be a value that is established (through engineering testing, system use testing, or prediction) that will prevent cutout for the target percentage of patients for the target amount of time (for example 95% of the patients will have 95% service (no cutouts) at $V_{rect,target}$ volts).

Figure 6:
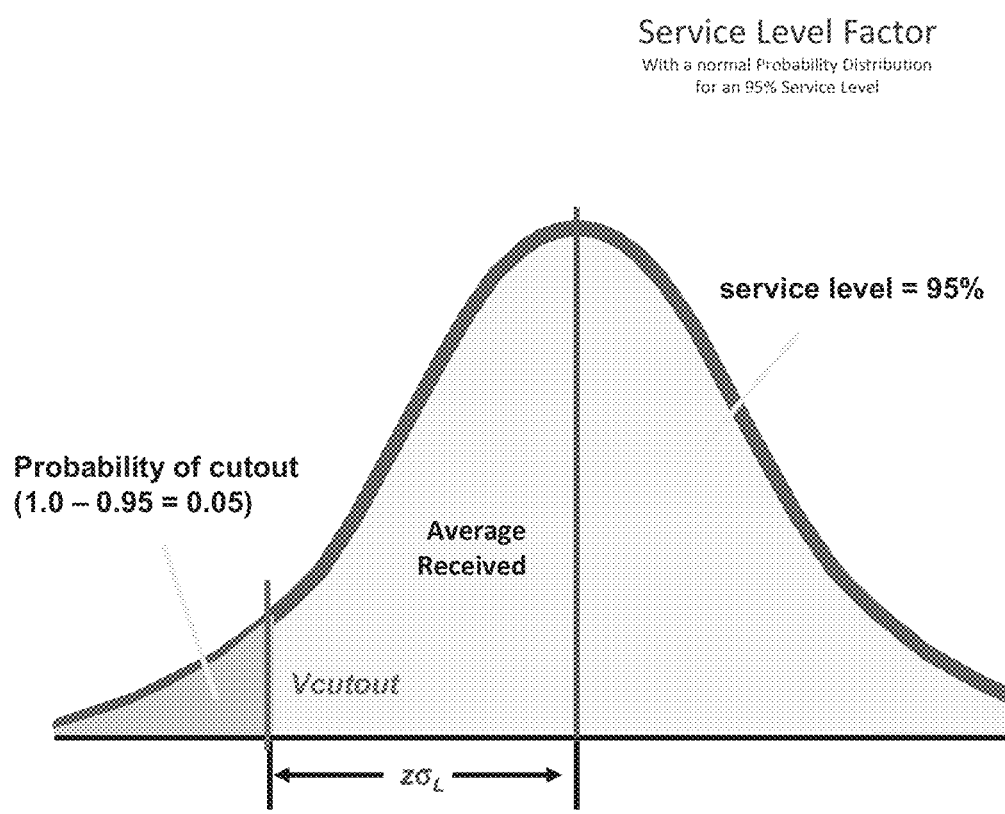
FIG. 6 is an example of a normal curve that can represents example values that can be used by the example parameter determination process.

Charging begins at the initial target $V_{rect,target}$. While adjusting charger output to maintain $V_{rect,target}$, a rolling average and standard deviation of reported values of $V_{rect,measured}$ from the IMD is monitored and maintained 4002. The target set point $V_{rect,target}$ is set to a value based on the minimum cutout value for $V_{rect,min}$ plus an overhead value that is proportional to the variability of the last n measured values: $V_{rect,target}=V_{rect,min}+X_{service}*(\sigma_{rect})$ where $X_{service}$ is a service factor corresponding to a current service level, and $\sigma_{rect}$ is the standard deviation of the previous n measurements. In normal distributions, $X_{service}$ can be the "z" variable (see FIG. 6, showing a normal distribution example for supporting a 95% service level).

The service factor $X_{service}$ determines the percentage of the time the measured power would fall below the minimum required power if received power followed a normal distribution. For example, if $X_{service}$ was 0, the power received would fall beneath the minimum 50% of the time while $X_{service}$ of 3 would correspond to approximately 1% chance of cutout in a perfectly normal distribution. Service level may be chosen based on current conditions (status) of the medical device (or its battery), such as a delta between current temperature and the maximum safe temperature, (i.e. at high temperatures decrease $X_{service}$ to avoid excess heat generation and at low temperatures increase $X_{service}$ to reduce cutouts). Thus, the service factor $X_{service}$ is adjusted according to the desired service level 4003. In cases where the current conditions would lead to a desire to widen the standard deviation (such as when the user is actively using the medical device, for example), a fractional value of $X_{service}$ might be used. Monitoring IMD temperatures and temperature impact on controlling the charging profile are discussed in more detail in co-pending U.S. patent application Ser. No. 13/607,037 filed concurrently with this application and incorporated herein by reference.

As the value of $\sigma_{rect}$ changes over time, the method compares the previous target value (e.g., $V_{rect,target}$) to the current desired target level 4004. If the target is determined to be off from its optimum, the target value is increased 4006 or decreased 4005 to obtain the new target (e.g., an updated $V_{rect,target}$). $V_{rect,measured}$ is then compared to the updated $V_{rect,target}$ 4007 to determine whether the power level of the external charger 3000 should be adjusted 4008. The system can the wait some time interval 4009 before continuously repeating the cycle 4010.

Note that although this process is clearly adapted to update the target values (e.g., by adjusting the transmitted power) for the slow-loop control based on variability of the rectified voltage, it can instead or concurrently be used to update the target values for the load on the primary coil 301 as well, as the target values can be similarly increased or decreased based on the historical measurements of the load in a similar manner as described above. More complex control can also be implemented by using multiple target variables, such as both $V_{rect}$ and reflected loads at the same time, or by adjusting the target values of the slow-loop control as well. The use of variability in reflected load to set $V_{RECT}$ can also be utilized. Finally, on an implant that allows variable rates of charging, the implant can be forced to a lower charging rate when the targeted $V_{rect,target}$ is greater than a threshold that quickly leads to excessive heating.

Hence, this method can be used to adapted the level of power transmitted by the external charger based on any number of monitored conditions, such as those typically found in the medical device, but also those that might be found in the external charger itself. Hence, this approach can be used to best optimize the charging process, while protecting the patient, based on actual conditions being observed in the devices.

The above control approach can be used for charging batteries in many different devices even outside the medical field, and even those devices that are connected to their charges in a non-wireless manner. Such an approach can be useful in controlling the charging process to increase battery lifetimes by preventing life-shortening charging conditions, such as charging the battery too fast, overcharging, or otherwise improperly charging the battery, in whatever type of device the battery is used.

Many other example embodiments can be provided through various combinations of the above described features. Although the embodiments described hereinabove use specific examples and alternatives, it will be understood by those skilled in the art that various additional alternatives may be used and equivalents may be substituted for elements and/or steps described herein, without necessarily deviating from the intended scope of the application. Modifications may be necessary to adapt the embodiments to a particular situation or to particular needs without departing from the intended scope of the application. It is intended that the application not be limited to the particular example implementations and example embodiments described herein, but that the claims be given their broadest reasonable interpretation to cover all novel and non-obvious embodiments, literal or equivalent, disclosed or not, covered thereby.

What is claimed is:

1. A method for charging a rechargeable battery in a medical device using an external charger, said method comprising the steps of:
    wirelessly transmitting a power signal from the external charger to the medical device, said power signal including power for charging the rechargeable battery;
    in the medical device, measuring a value of a first variable relating to the power signal received by the medical device from the external charger;
    transmitting the value of the first variable from the medical device to the external charger concurrent with wirelessly receiving the power signal;
    in the external charger, measuring a value of a second variable relating to the power signal transmitted by the external charger to the medical device; and
    adjusting the power signal transmitted from the external charger to the medical device at least partly based on values of both said first variable and said second variable.

2. The method of claim 1, wherein the value of said first variable is wirelessly transmitted to said external charger by said medical device.

3. The method of claim 2, wherein said step of adjusting includes the steps of: said external charger calculating an updated power signal for transmitting to said medical device using said first variable and said second variable; and said external charger transmitting said updated power signal to said medical device.

4. The method of claim 1, wherein said step of adjusting includes the steps of: said external charger calculating an updated power signal for transmitting to said medical device using said first variable and said second variable; and said external charger transmitting said updated power signal to said medical device.

5. The method of claim 1, wherein said step of adjusting includes the steps of:
    over a first time interval, calculating a power of the power signal transmitted from the external charger to the medical device based on a value of said second variable; and
    receiving a value of said first variable from the medical device regularly over a second interval longer than said first interval, wherein
    when a value of the first variable is received from the medical device, the step of calculating the power of the power signal transmitted is adjusted according to the value of the first variable as compared to a target value for the first variable.

6. The method of claim 5, wherein the amount that the step of calculating the power is adjusted is based on a standard deviation of a historical accumulation of values of the first variable.

7. The method of claim 5, wherein the amount that the step of calculating the power is adjusted is based on a standard deviation of a historical accumulation of values of the first variable multiplied by a factor based on a status of the medical device.

8. The method of claim 1, wherein said first variable is a measurement of a rectified voltage in the medical device and wherein said second variable is a power of the power signal transmitted by the external charger based on a measurement of the voltage and current provided at an output of the external charger.

9. The method of claim 1, wherein said medical device is an implantable medical device for implanting in the body of a patient for performing electrical stimulation and wherein said external charger is provided outside of the body of the patient for inductively transmitting power to said medical device using the power signal.

10. A system for implementing the method of claim 1, comprising the external charger and the medical device.

11. A method for charging a rechargeable battery in an implantable medical device using an external charger, said method comprising the steps of:
    inductively transmitting power from a primary coil of the external charger to a secondary coil of the medical device;

in the medical device, measuring a value of a rectified voltage of the secondary coil obtained from the power received from the external charger;

periodically transmitting the value of the rectified voltage or a derivation thereof from the medical device to the external charger;

in the external charger, determining a value of the power transmitted by the external charger to the medical device; and in the external charger, adjusting the power transmitted from the external charger to the medical device at least partly based on the determined value of the power transmitted by the external charger to the medical device, wherein when the value of the rectified voltage or derivation thereof is received by the external charger, the step of adjusting the power transmitted from the external charger to the medical device is based on the value of the rectified voltage or derivation thereof as compared to a desired value.

12. The method of claim 11, wherein said desired value is determined from a standard deviation of a number of values of the rectified voltage or the derivation thereof.

13. The method of claim 11, wherein said desired value is determined from a standard deviation of a number of values of the rectified voltage, or the derivation thereof, multiplied by a factor based on a status of the medical device.

14. The method of claim 11, wherein said step of transmitting the value of the rectified voltage or the derivation thereof is done via the inductive link between the external charger and the medical device.

15. The method of claim 11, wherein said step of transmitting the value of the rectified voltage or the derivation thereof is done via an RF link between the external charger and the medical device.

16. A system for implementing the method of claim 11, comprising the external charger and the medical device.

17. A method for charging a rechargeable battery in an implantable medical device using an external charger, said method comprising the steps of:

inductively transmitting power from a primary coil of the external charger to a secondary coil of the medical device;

in the medical device, measuring a first variable representing the power received from the external charger;

periodically transmitting the value of the first variable from the medical device to the external charger;

in the external charger, determining a value of a second variable representing the power transmitted by the external charger to the medical device;

in the external charger, adjusting the power transmitted from the external charger to the medical device at least partly based on the determined value of the second variable; and in the external charger, statistically analyzing a plurality of the values of the first variable received from the medical device, wherein when the value of the first variable is received by the external charger, adapting the step of adjusting the power transmitted from the external charger to the medical device based on the value of the rectified voltage as compared to a desired value of the rectified voltage that is determined at least partly based on a result of the statistically analyzing step.

18. The method of claim 17, wherein said adapting said adjusting the power transmitted from the external charger to the medical device step is also based on a status of the medical device.

19. The method of claim 17, wherein said step of statistically analyzing includes the step of determining a standard deviation of the plurality of the values of the first variable, and wherein the desired value of the rectified voltage is determined at least partly based on the determined standard deviation.

20. A system for implementing the method of claim 17, comprising the external charger and the medical device.

21. A method of providing a neurostimulation therapy to a patient, comprising the steps of:

providing an implantable medical device having a rechargeable battery and being implanted in a patient;

using said implantable medical device for driving at least one electrode implanted in the patient to stimulate at least one nerve of the patient; and recharging said battery using an external charger, said recharging including the steps of:

wirelessly transmitting power from the external charger to the medical device;

in the medical device, measuring a value of a first variable relating to the power received by the medical device from the external charger;

in the external charger, measuring a value of a second variable relating to the power transmitted by the external charger to the medical device; and adjusting the power transmitted from the external charger to the medical device at least partly based on values of both said first variable and said second variable.

22. A method for charging a rechargeable battery in a medical device using an external charger, said method comprising the steps of:

wirelessly transmitting an inductive power signal from the external charger to the medical device, said power signal including power for charging the rechargeable battery;

in the medical device, measuring a value of a first variable relating to the power signal received by the medical device from the external charger;

transmitting the value of the first variable from the medical device to the external charger using an RF transmission;

in the external charger, measuring a value of a second variable relating to the power signal transmitted by the external charger to the medical device; and adjusting, in the external charger, the inductive power signal transmitted from the external charger to the medical device at least partly based on values of both said first variable and said second variable.

* * * * *

UNITED STATES PATENT AND TRADEMARK OFFICE
CERTIFICATE OF CORRECTION

PATENT NO.        : 9,142,989 B2
APPLICATION NO.   : 13/606921
DATED             : September 22, 2015
INVENTOR(S)       : Fell et al.

Page 1 of 1

It is certified that error appears in the above-identified patent and that said Letters Patent is hereby corrected as shown below:

Title Page, Item (75) Inventor is corrected to read:
-- Roger Fell, Avon Lake (OH);
Benjamin Cottrill, Cleveland (OH);
Les Halberg, Valencia (CA);
Michael Labbe, Twinsburg (OH);
Joey Chen, Valencia (CA);
John Abraham, St. Paul (MN) --.

Signed and Sealed this
Fifth Day of April, 2016

Michelle K. Lee
*Director of the United States Patent and Trademark Office*